United States Patent [19]

Eguchi et al.

[11] 4,283,935
[45] Aug. 18, 1981

[54] DEVICE FOR MEASURING THERMAL CONDUCTIVITY OF LIQUID

[75] Inventors: Wataru Eguchi, Kyoto; Makoto Harada, Otsu; Masataka Tanigaki; Yutaka Tada, both of Kyoto, all of Japan

[73] Assignee: President of Kyoto University, Tokyo, Japan

[21] Appl. No.: 103,228

[22] Filed: Dec. 13, 1979

[30] Foreign Application Priority Data

Mar. 19, 1979 [JP] Japan ................................. 54-31911

[51] Int. Cl.$^3$ ............................................ G01N 25/18
[52] U.S. Cl. .................................................. 73/15 A
[58] Field of Search ...................... 73/15 A, 15 R, 530

[56] References Cited

FOREIGN PATENT DOCUMENTS 2331280 1/1975 Fed. Rep. of Germany .......... 73/15 A

OTHER PUBLICATIONS

Schnempf, "Thermal Diffusivity of Liquid Metals ...", Rev. Scien. Instr., vol. 43, No. 5 (1972), pp. 781-786.

*Primary Examiner*—Donald O. Woodiel
*Attorney, Agent, or Firm*—Robert E. Burns; Emmanuel J. Lobato; Bruce L. Adams

[57] ABSTRACT

A device for measuring thermal conductivity of a desired sample liquid, even of a transparent or hot sample liquid, on the basis of thermal diffusion to the sample liquid from a small and thin metal disc which is heated by laser flash. The device has means for elevating the relative surface level of the sample liquid, filling a gap between the metal disc and a sample holding block to form a cylindrical liquid layer therein, and the thermal diffusion can be measured by a thermocouple connected to the metal disc.

16 Claims, 12 Drawing Figures

DEVICE FOR MEASURING THERMAL CONDUCTIVITY OF LIQUID

BACKGROUND OF THE INVENTION

This invention relates to a device for measuring thermal conductivity of liquids under heating by impulsive light from a laser (laser flash), which is especially suitable for measuring thermal conductivity of hot melts.

In the conventional laser flash heating type measuring device of this class, a sample liquid, for instance, mercury is sealed in a container of boron nitride with a lid of transparent quartz plate and irradiated from above by a laser flash, while measuring the response in temperature rise at the bottom surface of the sample layer by a thermocouple which has its detecting end at the bottom of the container.

However, such conventional measuring device has the following problems.

(1) The measurement is possible only with an opaque liquid like mercury which is impermeable to laser light and which can receive the energy of the irradiated laser flash at its surface, and not with most of other liquids which are permeable to the laser light.

(2) Where a liquid of good thermal conductivity like a liquid metal is to be measured, it is easy to choose a container material with a thermal conductivity low enough as compared with that of the sample liquid. However, many of other liquids do not have much difference in thermal conductivity from the container which holds the sample, making it difficult to obtain the heat conductivity and thermal diffusivity of a sample from the measurement of its temperature response.

(3) It is extremely difficult to seal up the sample liquid in the container and a thin gas absorption layer is apt to be formed between the sample liquid and the wall surfaces of the container, producing a contact resistance which causes unignorable errors to the measured values.

(4) Strick assessment of the thickness of the sample liquid layer is required in analyzing the measured temperature response, so that it is necessary to known precisely the thermal expansion coefficient of the container for measurements at high temperatures. In addition, there is a possibility of the sample liquid overflowing from the container or of a void space being formed within the container when the measuring temperature is changed, due to the difference in thermal expansion coefficient between the container material and the sample liquid.

As for the conventional means for measuring thermal conductivity of hot melts, there have thus far been proposed a stationary means, a non-stationary hot-wire means and a non-stationary plate heating means.

The stationary means requires a long time for creating the stationary state and a high degree of expertness, with unavoidable heat losses to the ambient which cause greater errors to the measurement as the temperature is increased.

The non-stationary hot-wire means is considered to be reliable at temperatures below 500 K but its measuring device has a shape which cannot suppress the convection in the sample liquid and thus is unsuitable for the measurements at high temperatures.

The non-stationary plate heating means employs a horizontal plate which is immersed in a hot melt and to which current is applied stepwise or at a predetermined cycle to generate Joule heat. The curve of the temperature rise of the liquid is measured at a predetermined distance from the plate or the phase difference between the periodical variation of the liquid temperature and the cycle of the current flow through the plate is measured. In this case, it is also difficult to suppress the convection, coupled with a problem that the application of Joule heating to electrically conductive liquids by electric current necessitates a special contrivance for the insulation of the heating plate.

SUMMARY OF THE INVENTION

The present invention contemplates to solve the above mentioned problems and drawbacks and has as its object the provision of a device for measuring thermal conductivity of liquids, which is capable of absolute measurement of thermal conductivity of liquids or liquidus materials, including light permeable and electrically conductive liquids with ordinary or relatively low thermal conductivity, in a quick and facilitated manner without use of any reference material and without requiring strict assessment of the thickness of the sample liquid layer.

It is another object of the present invention to provide a device which is easily applicable to the measurement of thermal conductivity of hot liquid melts.

According to the present invention, there is provided a device for measuring thermal conductivity of liquids, characterized by the provision of: a horizontally supported, thin and small metal disc to be heated by a laser flash; a sample holding block located beneath the metal disc; a thermocouple connected to the metal disc; and a means for elevating the relative surface level of the sample liquid, filling a gap between the metal disc and sample holding block to form a cylindrical liquid layer therein.

The measuring device according to the present invention is capable of absolute measurement of thermal conductivity of liquids in general without using any reference material over a wide temperature range and in a quick and simple manner, including light transmissive liquids, electrically conductive liquids, liquids of normal thermal conductivity and liquidus hot melts which have been difficult to be handled by the conventional measuring devices.

According to another aspect of the present invention, there is provided a device for measuring thermal conductivity of liquids, characterized by the provision of means for removing air bubbles from the sample liquid to fill the gap between the metal disc and the sample holding block for the formation of a cylindrical liquid layer.

Therefore, in the measuring device of the present invention, a cylindrical layer of the sample liquid is formed securely and easily in the gap between the metal disc and the sample holding block.

BRIEF DESCRIPTION OF THE DRAWINGS

The accompanying drawings show by way of example a preferred embodiment of the present invention, in which.

DESCRIPTION OF PREFERRED EMBODIMENT

Figure 1:
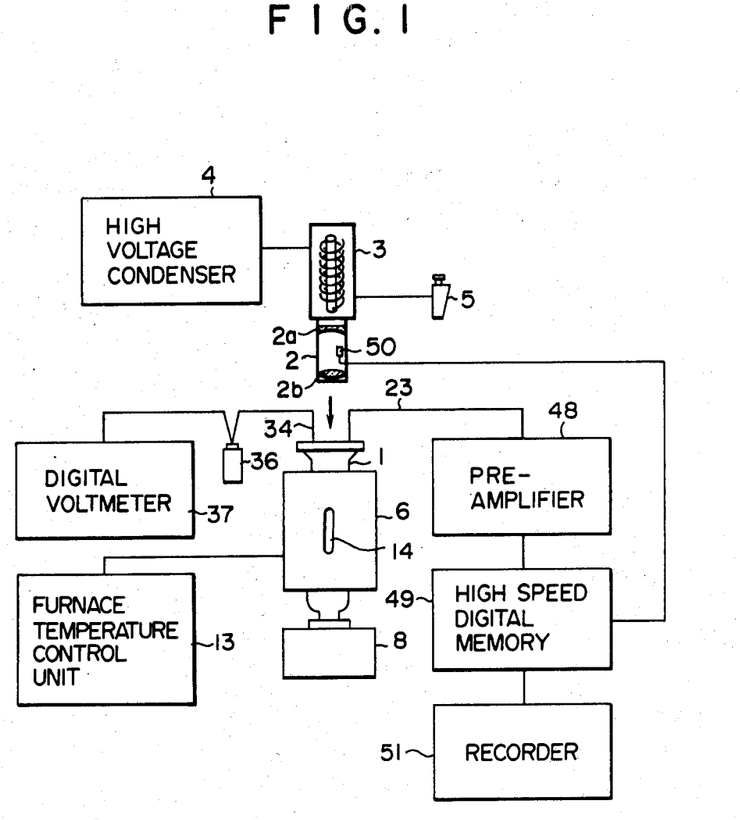
FIG. 1 is a diagrammatic view showing the general arrangement of a measuring device according to the present invention.

Referring to FIG. 1, the measuring device according to the present invention includes a sample chamber 1 and, overhead the sample chamber 1, a ruby laser beam generator 3 with a diametral beam magnifier 2. The ruby laser beam generator 3 irradiates the sample chamber 1 with an impulsive laser light from a monochrystalline ruby rod which is excited by discharging the electric energy stored in a high voltage condenser 4 to a xenon lamp through a remote switch 5.

The projected laser beam is diametrally magnified by the laser beam magnifier 2 which consists of a combination of a concave lens 2a and a convex lens 2b, thereby irradiating the sample chamber 1 with energy of uniform surface density.

Figure 2:
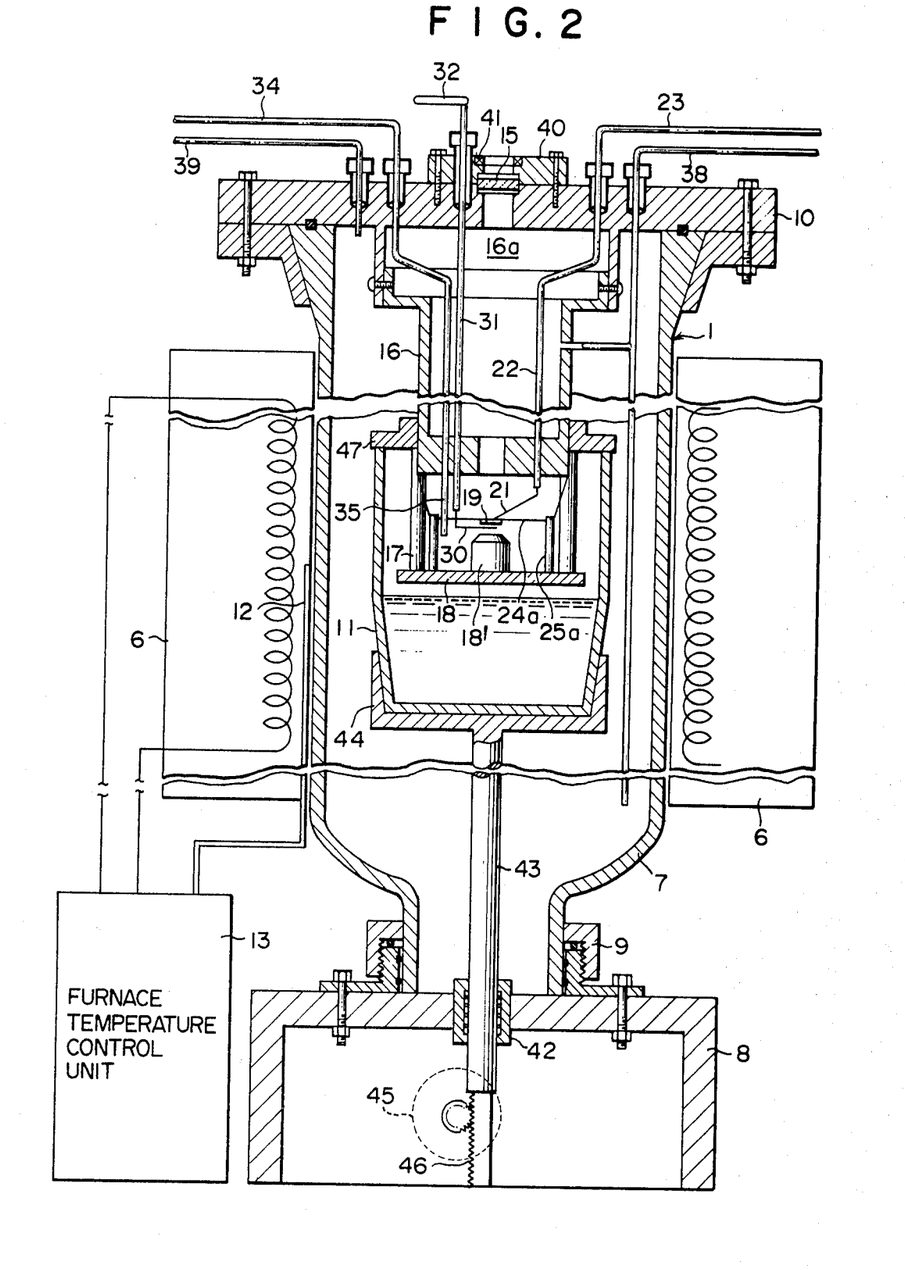
FIG. 2 is a diagrammatic vertical section showing on an enlarged scale the essential portions of the measuring device.

As shown in FIG. 2, the sample chamber 1 is constituted by a heat resisting mantle 7 of transparent quartz glass which is surrounded by an electric furnace 6, a mantle support table 8 which supports the bottom end of the mantle 7, and a mantle lid 10 which hermetically closes the top end of the mantle 7. A sample container of transparent quartz glass 11 is placed in the mantle 7 of the sample chamber 1. An O-ring packing and a gland 9 are provided between the bottom end of the mantle 7 and the mantle support table 8.

The temperature of the electric furnace 6 is detected by a furnace temperature measuring thermocouple 12 to apply current to the heater under PID control by a furnace temperature control unit 13, thereby controlling the temperature of the measuring atmosphere to a predetermined level. A view window 14 is provided in the wall of the electric furnace 6 to allow eye inspection of the conditions inside the container 11 through the mantle 7 (see FIG. 1).

The electric furnace 6 is of the non-inductive type to avoid errors of measurement.

The lid 10 of the mantle 7 is centrally provided with a circular window of optical glass 15 to allow passage therethrough of the incident laser beam. The lid 10 is provided with a coaxial guide member 16 in the form of a hollow cylinder forming a passage 16a to direct the laser beam which comes in through the optical glass window 15 to a small metal disc 19.

Attached to the lower end of the guide member 16 are three posts 17 which support a sample liquid support plate 18 at the lower ends thereof.

Figure 3:
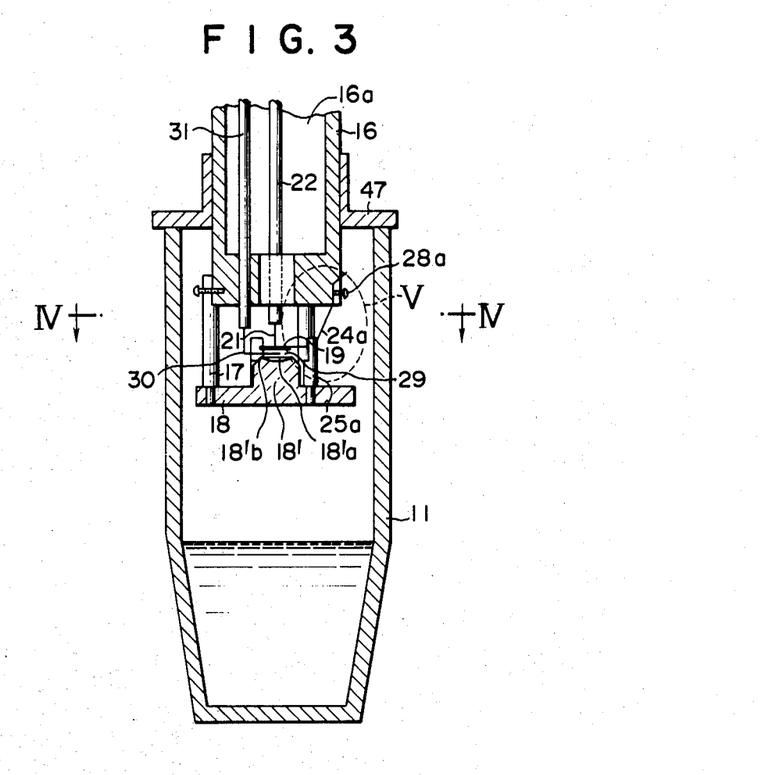
FIG. 3 is a vertical section also showing the essential portion on an enlarged scale.
Figure 4:
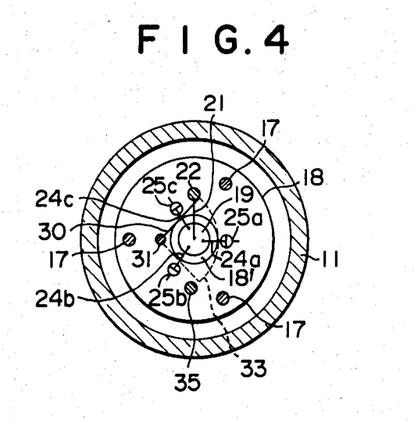
FIG. 4 is a horizontal section taken on line IV—IV of FIG. 3.

The sample liquid support plate 18 is secured to the guide member 16 by fixing its posts 17 to the lower end of the guide member 16 by means of screws, as shown in FIGS. 3 and 4. As a result, the sample holding plate 18 is coaxially suspended from the guide member 16.

Figure 5:
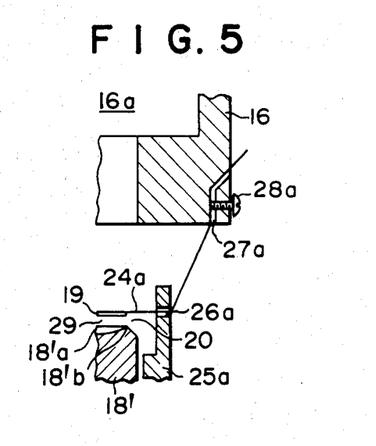
FIG. 5 is a fragmentary vertical section showing on an enlarged scale the encircled portion V in FIG. 4.

The sample liquid holding plate 18 is centrally provided with a coaxial sample holding block 18' which has a depression 18'a in the form of a shallow saucer as shown in FIG. 5, the circumferential portions of the saucer being cut in a tapered fashion to form an annular ridge 18'b on the top surface of the sample holding block 18'.

Located above the sample holding block 18' is a thin and small metal disc 19 which has the same diameter as the annular ridge 18'b and which is supported in a horizontal position with its lower surface spaced from the crest of the annular ridge 18'b by a gap 20 of 1 to 2 mm.

In other words, the sample holding block 18' is provided beneath the horizontally supported metal disc 19.

As shown in FIGS. 2 to 4, a thermocouple 21 is connected by welding to the center of the upper surface of the metal disc 19 for the detection of the temperature on the upper surface of the metal disc 19, the thermocouple 21 being sheathed in an insulator pipe 22 which is passed through the guide member 16 and the mantle lid 10 for connection to a sheathed lead wire 23 outside the sample chamber 1.

The small metal disc 19 is supported in the horizontal position by three metal filaments 24a, 24b and 24c which are spot-welded to the upper surface of the disc 19, as shown in FIG. 4, and fixed by screws to the lower portions of the guide member 16 through small holes in the three posts 25a, 25b and 25c which are secured to the sample holding plate 18. More particularly, as shown in FIG. 5 the metal filament 24a is passed through the small hole 26a in the post 25a and then through a small hole 27a at the lower end of the guide member 16 and fixed therein by a screw 28a. The other two metal filaments 24b and 24c have the respective outer ends fixed in the same manner. In this connection, the tension of the three metal filaments should be adjusted carefully such that the metal disc 19 is supported securely in a horizontal position coaxial with the sample holding block 18'.

A gap 29 between the metal disc 19 and the sample holding block 18' is provided to form a cylindrical liquid layer 53 of the sample. In order to remove the air bubbles which impede the filling of the sample liquid 52 in the gap 29, there is provided a bubble removing means or a stirrer member including a stirring scull 30 in the form of an L-shaped filament which is disposed within the gap 29.

The stirrer member further includes a vertical shaft 31 which supports the stirring scull 30. As shown in FIG. 2, the vertical shaft 31 is led out of the sample chamber 1 through the guide member 16 and the mantle lid 10 and provided with an operating handle 32 at the upper end thereof. Upon manipulating the handle 32 from outside, the stirring scull 30 is rotated reciprocatingly in the sectoral angular range 33 shown in FIG. 4.

In order to measure the temperature within the sample container 11, a thermocouple 34 is inserted into the sample container 11 through the lid 10 of the mantle 7 and the guide member 16 as shown in FIG. 2.

The lower portion 35 of the thermocouple 34 which is projected into the sample container 11 from the lower end of the guide member 16 is protected by a quartz tube and has its distal end positioned sideward of the annular ridge 18'b of the sample holding block 18'.

As seen in FIG. 1, the thermocouple 34 is connected to a zero-setting ice jar 36 and a digital voltmeter 37 by sheathed thermocouple lead wire.

Further attached to the mantle lid 10 are a gas inlet pipe 38 through which an inert gas is admitted into the sample chamber 1 and a gas exhaust pipe 39 through which a gas within the sample chamber 1 is discharged, as shown in FIG. 2.

The mantle lid 10 is hermetically sealed by a packing and a gland where it receives the insulator pipe 22 for the thermocouple 21 which measures the temperature at the upper surface of the small metal disc 19, the thermocouple 34 which measures the temperature within the sample container, the rotatable shaft 31 of the stirrer 30, the gas inlet pipe 38 and the gas exhaust pipe 39.

An annular auxiliary heater 41 is provided in a position proximal to the optical glass window 15, more particularly, on a window frame 40 which holds the optical glass in position, for the purpose of preventing dimming of the optical glass due to condensation of vapors of the sample liquid on the inner surface of the glass.

As shown in FIGS. 2 and 3, the sample container 11 generally has a cylindrical shape with its lower portions tapered toward a flat bottom and is made of a transparent quartz material so that one can view the conditions within the container through the view window 14 in the electric furnace 6 shown in FIG. 1.

The sample container 11 is placed on a tray 44 which is mounted on top of a lifting column 43 which is in turn movably erected on the mantle support table 8 through a mechanical seal 42, as shown in FIG. 2.

The lifting column 43 is moved up and down by turning a handle 45 which is connected to a drive mechanism including a rack 46 formed at the lower end of the lifting column 43, thereby moving the sample container 11 upward or downward within the mantle 7 of the sample chamber.

The lid 47 of the sample container 11 is slidably fitted on the guide member 16, so that the lid 47 is slided along the guide member 16 when the sample container 11 is moved upward or downward by the lifting column 43, maintaining intimate contact with the container 11.

Thus, the means for lifting the relative surface level of the sample liquid is constituted by the guide member 16 which supports the small metal disc 19 and the sample holding block 18' at the lower end thereof and the sample container which accommodates the small metal disc 19 and the sample holding block 18' and which is movable relative to the guide member 16.

The signal from the thermocouple 21 which is spot-welded to the center of the small metal disc 19 is fed through the thermocouple lead wire 23 as shown in FIG. 1 to be stored in a high speed digital memory 49 after amplification by a preamplifier 48. The high speed digital memory 49 is constituted by two channels of memory one for the measurement of the response in a short time period (0–50 ms) and the other for the measurement of the response in a longer time period (variable in the range of 0–1 second or 0–5 seconds) and a memory scope.

The trigger signal for starting the high speed digital memory 49 is produced by a photodiode 50 which is located between the concave and convex lenses 2a and 2b of the laser beam magnifier 2. Upon detection of the incident laser beam, the photodiode 50 transmits a trigger signal to the high speed digital memory 49.

The data of the measured temperature response of the small metal disc 19 are later recorded by a recorder 51.

The small metal disc 19 to be subjected to the measurement of the temperature response under heating by a laser flash should be heat resistant and of good thermal conductivity with resistance to corrosion by the sample liquid. In addition, the metal disc 19 is preferred to have a thickness small enough but capable of maintaining flatness without machining distortion resulting from the spot-welding of the thermocouple 21 and the metal filaments 24a to 24c. For example, for the measurement of the thermal conductivity of a melt of a nitrate, a disc of high purity nickel with a thickness of 0.236 mm will be suitable.

It is preferred, if possible, to avoid the use of metallic component parts in the sample chamber 1 or it becomes necessary to ground each metallic part completely since otherwise there will be produced an inductive potential when a large current is applied for the excitation of the laser beam generator 3, causing erroneous noises to the values of measurement of the temperature response of the metal disc 19.

For the purpose of facilitating the location of the sample chamber 1, the electric furnace 6 is preferred to be a split type which is separable vertically into two halves.

In order to measure the thermal conductivity of a sample liquid with the measuring device of the invention as constructed above, the sample lifting handle 45 of the mantle support table 8 is operated in the first place to lower the container support tray 44 to its lowest position and then a sample container 11 which holds a predetermined quantity of the sample 52 is placed thereon.

In the next place, the mantle 7 of quartz material is mounted in position, securing its lower portion to the support table 8 by means of the gland 9 and closing on the mantle 7 the lid 10 which has the necessary parts set therein, including the sample support plate 18 with the sample holding block 18', the small metal disc 19, the thermocouple 21 for measuring the surface temperature, the thermocouple 34 for measuring the inner temperature of the sample container, the shaft 31 with the stirrer 30 of L-shaped filament, the guide member 16, the gas inlet pipe 38, the gas exhaust pipe 39 and the optical glass window 15.

Figure 6A:
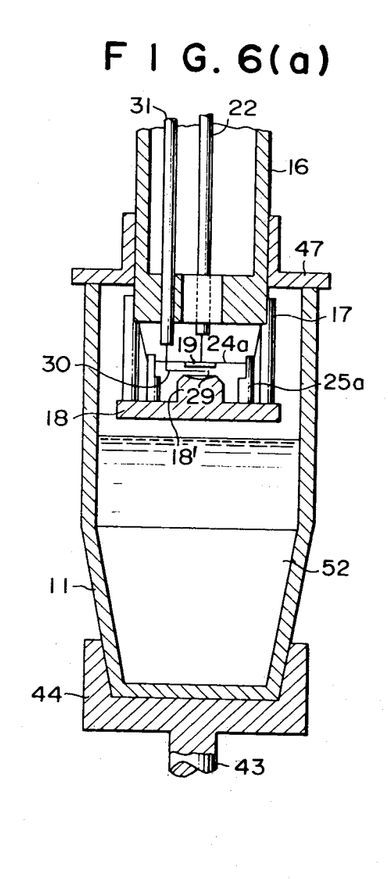
FIGS. 6(a) to 6(c) are fragmentary vertical sections employed for the explanation of its operation.

Under these circumstances, the inside of the sample container 11 is in the conditions as shown in FIG. 6(a). The respective parts of the sample chamber 1 are dimensioned such that the lower side of the sample holding plate 18 does not come into contact with the sample 52 in the container 11.

After fixing the mantle 7 in this manner, the electric furnace 6 is mounted in position and the wires of the thermocouples 21 and 34 are connected to the lead wires of the measuring circuit.

The gas inlet pipe 38 and the gas exhaust pipe 39 are connected respectively to the gas feed and exhaust pipings, and an inert gas is fed to the mantle 7 to replace the inside of the mantle with the inert gas.

Thereafter, the electric furnace 6 is turned on to start heating, raising the temperature within the mantle 7 until the temperature within the sample container 11 reaches the predetermined measuring temperature level.

In the meantime, the supply of the inert gas is stopped from time to time, while extracting the gas from the mantle 7 by a vacuum pump to reduce the pressure.

Then the inert gas is admitted again into the mantle 7 while blocking the gas exhaustion until the predetermined pressure for measurement is restored. This operation is repeated for several times.

This repeated pressurization and pressure reduction serves to replace the atmospheric gas in the mantle 7 with the inert gas and at the same time to deair the sample liquid by removing fine air bubbles which are formed when a sample material in the form of solid powder at room temperature is melted into a liquidus state as the temperature within the sample container is raised.

The gas resulting from the deairing of the melt in the sample container 11 is released by raising the container lid 47 which is fitted on the guide member 16.

In the last place, the valves (not shown) which are provided in the inert gas inlet pipe 38 and the gas exhaust pipe 39 are closed completely, and the measuring device is left to stand for a little while after adjusting the furnace temperature control unit 13 to a desired measuring temperature level.

The auxiliary heater 41 which is provided immediately above the optical glass window 15 is turned on in a case where the window is dimmed due to condensation of the sample liquid on the inner surface of the optical glass.

As a result of these preparatory operations, an inert gas atmosphere is created in the upper space of the sample chamber 1, which is saturated with vapors of the sample liquid.

Nextly, the laser beam generator 3 is positioned overhead the sample chamber 1, taking aim through the optical window 15 at the small metal disc 19 within the sample container 11. The remote switch 5 is then actuated to excite the ruby laser beam generator 3 by the electric energy charged in the high voltage condenser 4, generating an impulsive laser light.

The incident laser light is detected by the photodiode 50 and a trigger signal is fed to the high speed digital memory 49.

In this instance, the laser light from the ruby laser beam generator 3 undergoes diametral magnification through the laser beam magnifier 2, so that only the center portion of the beam with uniform surface density of energy is passed through the window 15 of the sample chamber 1 to irradiate the upper surface of the metal disc 19.

It has been confirmed by an experiment that the center portion of the diametrally magnified laser beam has a uniform surface density of energy. The experiment was directed to the study of temperature response at the back side of the metal disc 19 which is irradiated by the laser beam. As a result, there was obtained a response curve (FIG. 7) which monotonously converged to a maximum value without showing any locally increased values.

Figure 7:
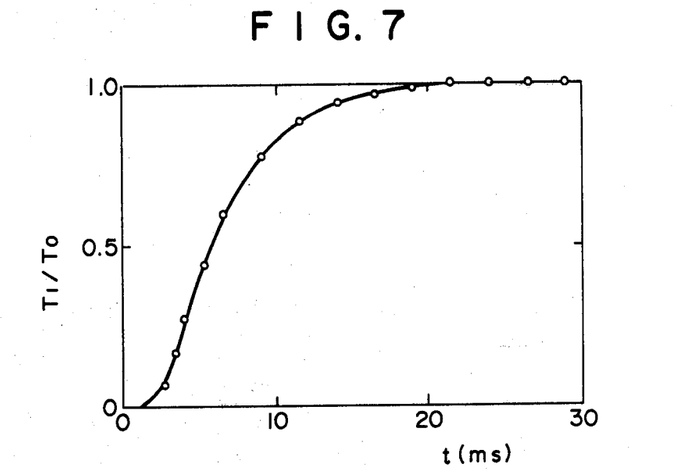
FIG. 7 is a graph plotting the temperature response at the back surface of the small metal disc.

It is known from the curve that the incident energy density in the center portion of the laser beam is uniform and it becomes possible to make data analysis on the basis of the principle of measurement of one dimensional thermal flow (which will be discussed hereinlater).

Upon irradiation by the laser light with uniform surface density of energy, the upper surface of the metal disc 19 is heated instantaneously but the heat rapidly diffuses over the entire body of the metal disc 19. As a result, the surface temperature of the metal disc 19 drops quickly and the disc 19 becomes to have a uniform temperature within an extremely short period of time of less than 10 ms. Therefore, the heat radiation of the metal disc 19 to the ambient atmosphere during such a short time period can be ignored.

Thereafter, the heat accumulated in the metal disc 19 is radiated to the ambient atmosphere very slowly, lowering the temperature of the disc 19 little by little.

The changes in the surface temperature of the metal disc 19 after the irradiation by the laser light are detected by the thermocouple 21, which is spot-welded to the upper surface of the metal disc 19, and the detected signals are amplified by the preamplifier 48 and stored in the digital memory 49. The stored temperature response is recorded on the recorder 51.

Figure 8:
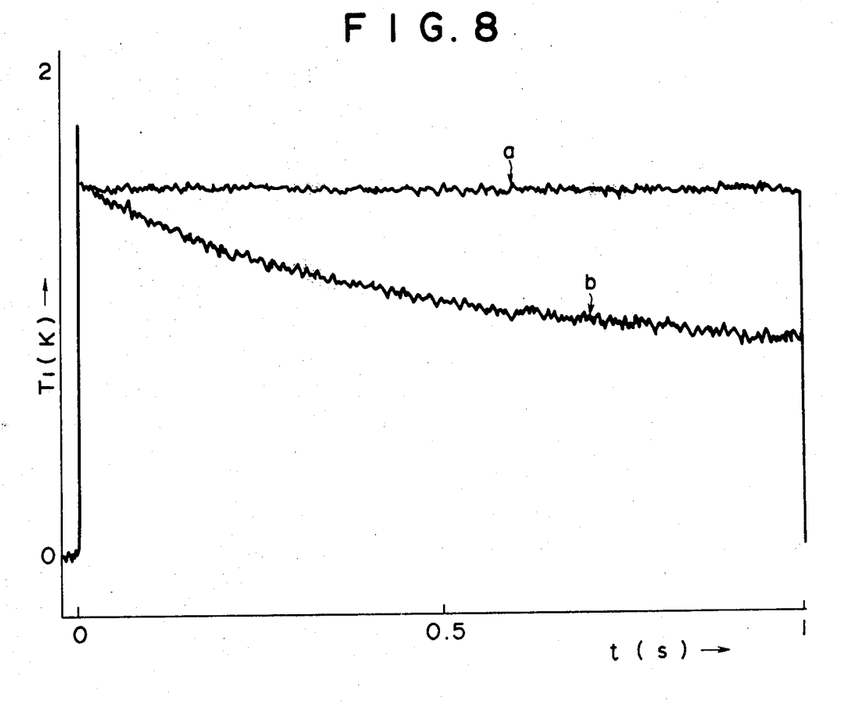
FIG. 8 is a graph plotting the temperature response on the upper surface of the small metal disc.

The upper curve a in FIG. 8 is a plot of the records of measurement as obtained by using a metal disc of high purity nickel, 6.55 mm in diameter and 0.236 mm in thickness.

Since the sample chamber 1 is maintained at a predetermined constant temperature, the temperature of the small metal disc 19 soon returns to the level same as the sample chamber 1.

Figure 6B:
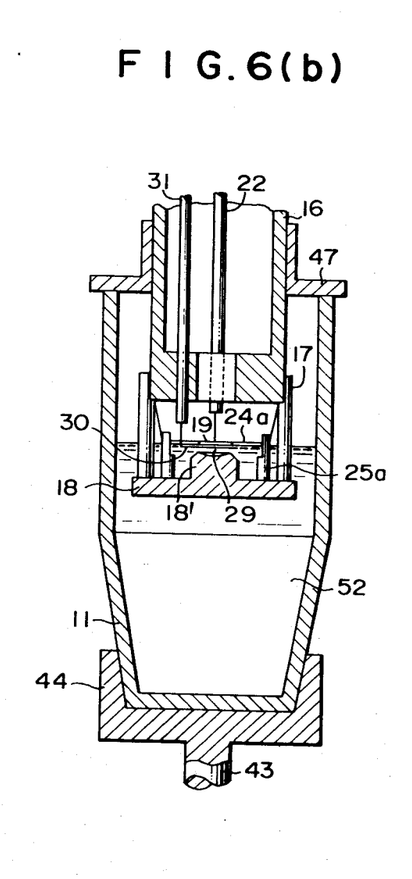

In the next place, the lifting handle 45 for the container support column 43 is rotated to lift the sample container 11 slowly to the position of FIG. 6(b) where the surface of the liquidus melt reaches just the underside of the small metal disc 19, allowing the sample liquid 52 to enter and fill the gap 29 between the metal disc 19 and the sample holding block 18'.

At this time, the L-shaped stirrer 30 is reciprocatingly oscillated in the sectoral range shown in FIG. 4 to urge the entrance of the sample liquid 52 which sometimes fails to due to its surface tension and to purge small air bubbles which tend to linger beneath the small metal disc 19, thereby completely filling the gap 29 with the sample liquid 52.

As soon as the gap 29 is completely filled with the sample liquid 52, the stirrer 30 is returned to its rest position at one side of the sectoral range or in a position outside the gap 29.

Figure 6C:
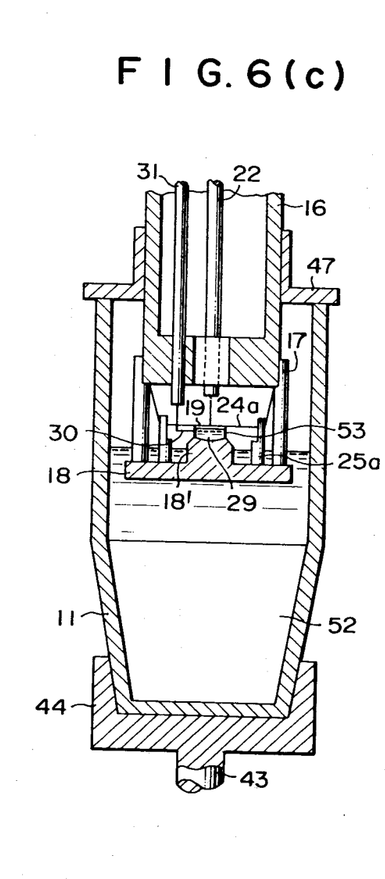

Then, the lifting handle 45 of the container support column 43 is turned slowly to lower the sample container 11 to the position of FIG. 6(c), whereupon a cylindrical liquid layer 53 is formed in the gap 29 between the small metal disc 19 and the sample holding block 18'.

The above-described operation of forming the cylindrical liquid layer 53 in the gap 29 between the metal disc 19 and the sample holding block 18' by lifting and lowering the sample container 11 can be performed while carefully watching the conditions within the sample container 11 in the mantle 7 through the view window 14 in the electric furnace 6, so that there occurs no change in the temperature within the sample container 11 during this operation.

After forming in the gap between the small metal disc 19 and the sample holding block 18' a cylindrical liquid layer 53 which has the same diameter as the metal disc, the metal disc 19 is again flash-irradiated by the laser beam to measure the temperature response at the upper surface of the disc 19.

The lower curve b of FIG. 8 is a plot of the temperature response obtained by laser-flashing a nickel disc 19 as used for the curve a, but with a cylindrical layer of melt sodium nitrate formed thereunder.

The thermal conductivity of the liquid 52 which fills the gap 29 between the metal disc 19 and the sample holding block 18' is calculated from the difference between the two laser-flash response curves a and b.

The thermal conductivity of sodium nitrate obtained from the analysis of the response curves a and b is shown in the following table in comparison with the recommended value.

| Sample | Measuring Temp. (K.) | Metal Disk | Thermal Conductivity (cal/(cm.s.K.)) Actual Value | Recommended Value |
|---|---|---|---|---|
| Sodium nitrate | 603 | High purity nickel | $1.30 \times 10^{-3}$ | $1.32 \times 10^{-3}$ |

Given hereunder is a practical procedure for obtaining the thermal conductivity of a liquid, treating the thermal flow as a problem of one dimentional diffusion.

Figure 9:
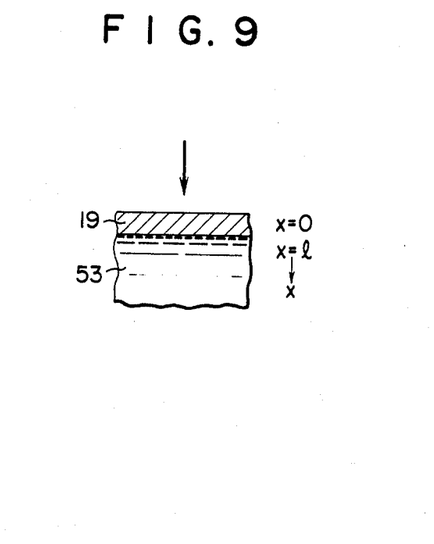
FIG. 9 is a diagrammatic view explanatory of its operation.

As shown in FIG. 9, if the metal disc 19 is considered as a first layer, a distance measured downwardly from the upper surface of the metal disc 19 is x, the thickness of the metal disc 19 is l, the cylindrical liquid layer 53 is considered as a second layer, and the gas layer above the first layer is considered as a third layer, we obtain the equations for the temperature responses at the upper and lower surfaces of the first layer (metal disc 19) or at x=0 and x=from the equation of thermal diffusion, initial condition and boundary condition, as follows.

$$\frac{T_1(O, t)}{T_0} = \int_0^t \tilde{f}(t - \tau) F_1(O, \tau) d\tau \tag{1-a}$$

$$F_1(O, \tau) = \frac{1}{\pi^{\frac{1}{2}}} \left(\frac{l^2}{\alpha_1 \tau}\right)^{\frac{1}{2}} \left[\frac{1}{1 + H_2} + \frac{2}{(1 - H_2)(1 + H_2)} \times \right. \tag{1-b}$$

$$\left. \sum_{n=1}^{\infty} \left(\frac{1 - H_1}{1 + H_1}\right)^n \left(\frac{1 - H_2}{1 + H_2}\right)^n \exp\left(-\frac{n^2 l^2}{\alpha_1 \tau}\right)\right]$$

$$\frac{T_1(l, t)}{T_0} = \int_0^t \tilde{f}(t - \tau) F_1(l, \tau) d\tau \tag{2-a}$$

$$F_1(l, \tau) = \left(\frac{1}{\pi^{\frac{1}{2}}}\right) \left(\frac{l^2}{\alpha_1 \tau}\right) \times \frac{2}{(1 + H_1)(1 + H_2)} \times \tag{2-b}$$

$$\sum_{n=0}^{\infty} \left(\frac{1 - H_1}{1 + H_1}\right)^n \left(\frac{1 - H_2}{1 + H_2}\right)^n \exp\left[-\frac{(2n + 1)^2 l^2}{4\alpha_1 \tau}\right]$$

Where $$H_1 \equiv \left(\frac{\lambda_2 \rho_2 C_{p2}}{\lambda_1 \rho_1 C_{p1}}\right)^{\frac{1}{2}} \tag{3}$$

$$H_2 \equiv \left(\frac{\lambda_3 \rho_3 C_{p3}}{\lambda_1 \rho_1 C_{p1}}\right)^{\frac{1}{2}} \tag{4}$$

$$T_0 \equiv \left(\frac{Q}{\rho_1 C_{p1} l}\right) \tag{5}$$

$$\tilde{f}(t) \equiv f(t)/Q \tag{6}$$

$$Q = \int_0^\infty f(t) dt \tag{7}$$

In the foregoing formulas, $T_1(x, t)$ is the difference between the temperature of the first layer at the distance x and at the time t and the temperature prior to the measurement, $\lambda_1, \lambda_2$ and $\lambda_3$ are the thermal conductivity of the first to third layers, respectively, $\alpha 1, \alpha 2$ and $\alpha 3$ are the thermal diffusivity of the first to third layers, respectively, and f(t) is a function which stands for the amount of energy as absorbed by unit area of the upper surface of the first layer.

Further, $C_{p1}, C_{p2}$ and $C_{p3}$ are the specific heat capacity of the first to third layers, respectively, $\rho_1, \rho_2$ and $\rho_3$ are the density of the first to third layers, respectively, and $T_o$ is a temperature rise which occurs on the assumption that the heat input to the first layer is uniformly stored therein without any scattering.

In the initial response, the equations (1-a), (1-b), (2-a) and (2-b) can be approximated by equations (8-a) and (9-a) under the condition of (8-b) and (9-b).

$$\frac{T_1(O, t)}{T_0} = \frac{1}{\pi^{\frac{1}{2}}} \cdot \frac{1}{1 + H_2} \int_0^t \left(\frac{l^2}{\alpha_1 \tau}\right)^{\frac{1}{2}} \tilde{f}(t - \tau) d\tau \tag{8-a}$$

Where $$\exp\left(-\frac{l^2}{\alpha_1 t}\right) << \left(\frac{1 + H_1}{1 - H_1}\right) \left(\frac{1 + H_2}{2}\right) \tag{8-b}$$

$$\frac{T_1(l, t)}{T_0} = \frac{2}{\pi^{\frac{1}{2}}} \cdot \frac{1}{(1 + H_1)(1 + H_2)} \int_0^t \left(\frac{l^2}{\alpha_1 \tau}\right)^{\frac{1}{2}} \times \tag{9-a}$$

$$\exp\left(-\frac{l^2}{4\alpha_1 \tau}\right) \tilde{f}(t - \tau) d\tau$$

Where $$\exp\left(-\frac{2l^2}{\alpha_1 t}\right) << \left(\frac{1 + H_1}{1 - H_1}\right) \left(\frac{1 + H_2}{1 - H_2}\right) \tag{9-b}$$

After the initial response, the following approximation can be established for the equations (1) and (2).

$$\frac{T_1(O, t)}{T_0} = \frac{T_1(l, t)}{T_0} = \exp(h^2 t) erfc(ht^{\frac{1}{2}}) \tag{10}$$

Where $$h = h_1 + h_2 \tag{11}$$

$$h_1 \equiv \frac{(\lambda_2 \rho_2 C_{p2})^{\frac{1}{2}}}{\rho_1 C_{p1} l} \tag{12-a}$$

$$h_2 \equiv \frac{(\lambda_3 \rho_3 C_{p3})^{\frac{1}{2}}}{\rho_1 C_{p1} l} \tag{12-b}$$

The foregoing proximate analysis shows that the thermal conductivity of the second liquid layer can be obtained by measuring the temperature drop $T_1(O, t)$ at the upper surface of the second layer and applying the measured value to the equation (10).

When determining the thermal conductivity $\lambda_2$ by the equation (10), the thermal conductivity $\lambda_1$ of the first layer is not required.

The liquids thermal conductivity measuring device of the present invention has the following effects or advantages.

(1) The sample liquid to be subjected to the measurement is in the form of a cylindrical liquid layer 53 filled in a 1 to 2 mm wide gap 29 between the small metal disc 19 and the sample holding block 18' in a diameter same as the metal disc 19 and its upper portion undergoes at maximum a temperature rise of 2 K. above the ambient temperature within the measuring time of less than 1 second, so that one can totally ignore the convection within the sample liquid layer during the measurement, thus ensuring measurements of extremely high accuracy. This is contrastic to the conventional hot-wire and plate heating means in which the measurement is apt to be influenced by the convection due to the shape of the sample liquid and its temperature distribution.

(2) The circumference of the thin cylindrical layer 53 of the sample liquid formed under the metal disc 19 is surrounded by the inert gas which is saturated with the vapors of the sample liquid, in contrast to the conventional means which necessitate to seal the sample liquid in a container. The conventional means involve a difficulty in assessing the measurement errors due to heat dissipation through the container walls. In the present invention, the heat dissipation to the surrounding gas phase is small enough.

(3) The errors of measurement due to heat dissipation can be known correctly from the data of laser-flash response of the metal disc 19 which is simply suspended in the atmospheric gas without forming the liquid layer thereunder, so that it becomes possible to effect the measurement with high accuracy.

(4) The sample to be subjected to the measurement is an extremely small quantity of liquidus material filled in the gap 29 between the metal disc 19 and the sample holding block 18' so that the sample can be easily maintained uniformly at a desired temperature prior to the measurement by the laser-flash.

(5) It becomes possible to effect absolute measurement without need for determining the constant of the device in relation with a reference material.

(6) The construction is advantageous to the measurement of thermal conductivity of liquid especially at high temperatures and applicable to higher temperatures as compared with the conventional measuring devices.

(7) The sample to be subjected to the measurement is placed in the sample container 11 which is liftable within the mantle 7 and shielded from the atmosphere. On the other hand, the metal disc 19 to be heated by the laser flash and the sample holding block 18' located under the metal disc 19 are fixedly supported on the mantle lid 10 through the guide member 16. With this construction, a cylindrical liquid layer 53 of the sample material is securely formed in the gap 29 between the metal disc 19 and the sample holding block 18' by the operation of lifting and lowering the sample container 11 and the stirring scull 30 which is oscillated in the gap 29.

(8) It becomes possible to measure the thermal conductivity of a wide range of liquidus materials, including a hot melt of a substance which is solid at room temperature, in addition to the measurement of the thermal conductivity of normally liquidus materials in the vicinity of room temperature.

In the foregoing embodiment, the means for lifting the relative surface level of the sample liquid is shown as consisting of a fixed guide member 16 and a sample container 11 which is movable relative to the guide member 16. However, it is possible to reverse relation of these two components such that the guide member is movable vertically relative to the sample container which is fixed.

Figure 10:
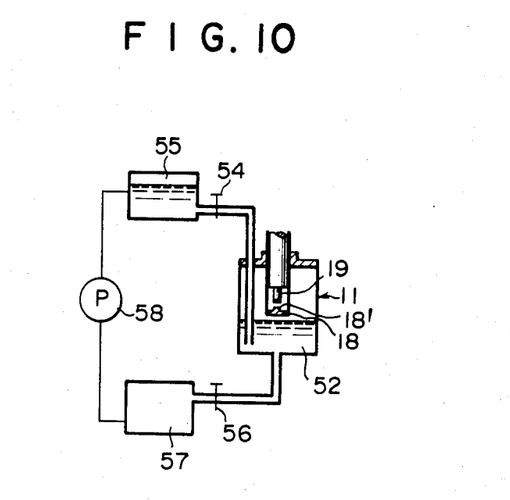
FIG. 10 is a diagrammatic view showing a modified embodiment of the means for lifting the relative surface level of the sample liquid.

Alternatively, as shown in FIG. 10, there may be provided a first tank 55 with a control valve 54 serving as means for supplying a sample liquid 52 to the container 11 and elevating its surface level, and a second tank 57 with a control valve 56 serving as means for discharging the sample liquid 52 from the container 11 to lower its surface level.

In this case, in order to supply the sample liquid 52 to the container 11 to elevate its surface level, the control valve 54 is opened to let the sample liquid 52 flow by gravity into the container 11 from the first tank 55. On the other hand, when it is desired to discharge the sample liquid 52 from the container 11 to lower its surface level, the control valve 56 is opened to let the sample liquid 52 in the container 11 flow by gravity into the second tank 57. The transfer of the sample liquid 52 from the second tank 57 to the first tank 55 is effected by a pump 58.

The arrangement shown in FIG. 10 is suitable for the measurement of thermal conductivity of liquids in the vicinity of room temperature.

What is claimed is:

1. A device for measuring thermal conductivity of liquids, characterized in that said device comprises:
   a horizontally supported, thin and small metal disc to be heated by a laser flash;
   a sample holding block located beneath said metal disc;
   a thermocouple connected to said metal disc; and
   means for elevating the relative surface level of a sample liquid, filling a gap between said metal disc and said sample holding block to form a cylindrical liquid layer therein.

2. A device as set forth in claim 1, characterized in that said elevating means comprises a guide member having at the lower end thereof said metal disc and said sample holding block, and a sample container enclosing said metal disc and said sample holding block and movable up and down relative to said guide member.

3. A device as set forth in claim 2, characterized in that said sample container is located in a heat resistant mantle to be heated by an electric furnace for melting a sample material in said container, and said guide member is pendently mounted on a lid of said mantle.

4. A device as set forth in claim 3, characterized in that said mantle and said sample container are made of a transparent quartz material and said electric furnace is arranged to surround said mantle and provided with a view window to allow eye inspection of the inside of said sample container through said mantle.

5. A device as set forth in claim 3, characterized in that said sample container is mounted on a lift member which is movable up and down within said mantle and connected at the lower end thereof to a lift drive mechanism.

6. A device as set forth in claim 3, characterized in that said mantle is provided with an optical glass window in the lid at the top end thereof for passing therethrough an incident laser beam and said guide member is provided with a passage for leading said incident laser beam toward said metal disc.

7. A device as set forth in claim 6, characterized in that an auxiliary heater is provided in the vicinity of said optical glass window to prevent dimming of said optical glass window.

8. A device as set forth in claim 2, characterized in that said sample container serves as a supply source of the sample liquid to fill said gap and a space to be saturated with vapors of said sample is provided around said metal disc and sample holding block.

9. A device as set forth in claim 1, characterized in that said sample holding block is provided with a depression in the form of a saucer on a surface opposing said metal disc, the circumferential portions of said depression being cut in a tapered fashion to form an annular ridge therearound.

10. A device as set forth in claim 9, characterized in that said annular ridge has the same diameter as and coaxial with said metal disc.

11. A device as set forth in claim 1, characterized in that said device further comprises a laser beam magnifier consisting of concave and convex lenses for diametrally magnifying the laser beam to be directed to said metal disc, thereby uniformalizing the density of incident energy.

12. A device as set forth in claim 1, characterized in that said elevating means comprises a sample container, a charging means for supplying the sample liquid to said sample container to elevate the surface level thereof, and a discharging means for discharging the sample liquid from said sample container to lower said surface level.

13. A device as set forth in claim 12, characterized in that said charging means includes a first tank with a control valve adapted to supply the sample liquid by gravity to said sample container, and said discharging means includes a second tank with a control valve adapted to discharge the sample liquid by gravity from said sample container.

14. A device for measuring thermal conductivity of liquids, characterized in that said device comprises:
- a horizontally supported, thin and small metal disc to be heated by a laser flash;
- a sample holding block located beneath said metal disc;
- a thermocouple connected to said metal disc; and
- means for removing air bubbles from a sample liquid filling a gap between said metal disc and said sample holding block to form a cylindrical liquid layer therein.

15. A device as set forth in claim 14, characterized in that said bubble removing means comprises a stirring member rotatingly movable into and out of said gap between said metal disc and said sample holding block.

16. A device as set forth in claim 15, characterized in that said stirring member is attached to the lower end of a vertical rotatable shaft having an externally operable lever at the upper end thereof.

* * * * *